United States Patent [19]

Tichy et al.

[11] 4,126,044
[45] Nov. 21, 1978

[54] ANTIFREEZE TESTER

[75] Inventors: Brian N. Tichy, Bloomington; Robert E. Clark, Minneapolis, both of Minn.

[73] Assignee: Thexton Manufacturing Company, Minneapolis, Minn.

[21] Appl. No.: 848,465

[22] Filed: Nov. 4, 1977

[51] Int. Cl.² ............................................. G01N 9/10
[52] U.S. Cl. ....................................... 73/440; 73/441
[58] Field of Search ........................ 73/440, 441, 448

[56] References Cited
U.S. PATENT DOCUMENTS

| 398,726 | 2/1889 | Hicks | 73/440 |
|---|---|---|---|
| 1,424,730 | 8/1922 | Linebarger | 73/440 |

Primary Examiner—Charles A. Ruehl
Attorney, Agent, or Firm—H. Dale Palmatier

[57] ABSTRACT

A specific gravity tester for antifreeze solutions including a transparent tube, a bulb on one end, and a sample-collecting hose on the other end; the transparent tube being of molded plastic and defining an interior guideway with broad, flat surfaces having projecting ribs to maintain the floats in spaced relation to the surfaces, the sidewalls of the tube having flat inner surfaces defining the guideway and rounded convex exterior surfaces to provide the sidewalls of the transparent tube with a magnifying lens characteristic.

10 Claims, 4 Drawing Figures

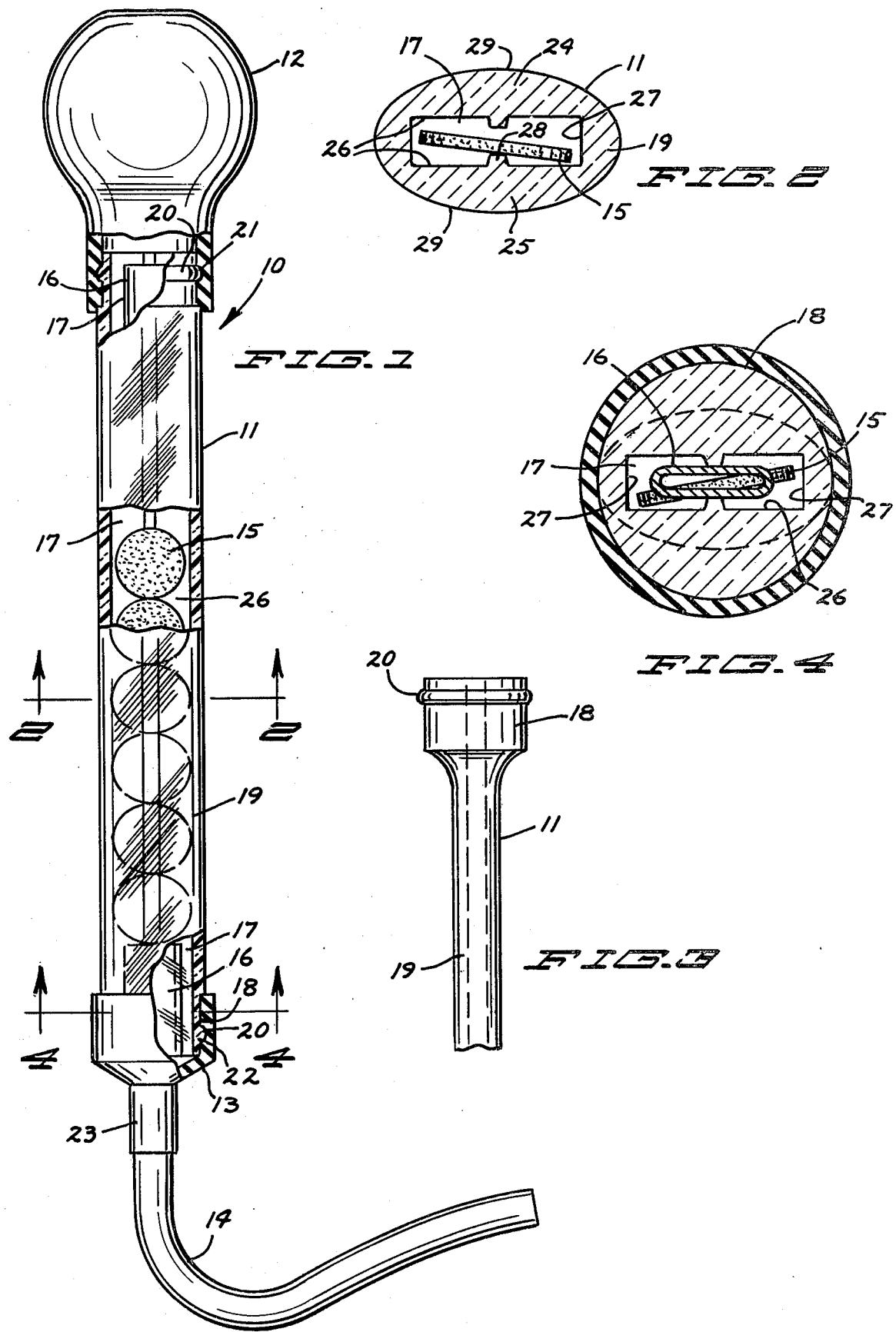

ANTIFREEZE TESTER

This invention relates to an antifreeze tester especially of the type used to check the antifreeze in the cooling system of an automotive type engine.

BACKGROUND OF THE INVENTION

It has been common practice for many years to test the strength of an antifreeze solution in the radiator of an automotive type engine by measuring the specific gravity of the solution. By determining the specific gravity of the solution, a conclusion can be reached as to the capability of the solution to withstand freezing at various temperatures.

Such a tester is basically a hydrometer, and such hydrometers have been in common usage for testing the specific gravity of many different liquids such as battery acid, as well as radiator cooling solutions consisting of ethylene glycol and water. Such hydrometers have even been used for testing the potency of alcoholic beverages and mixed drinks.

Such hydrometers, in recent times, have taken the form of a transparent tube into which a sample of the radiator solution is drawn. Oftentimes a short length of flexible rubber hose is attached to one end of the transparent tube, and a rubber bulb is provided on the other end of the tube in order to provide a suction effort for drawing a sample of the radiator solution into the transparent tube. The transparent tube has contained a number of small balls or wafers, each of which has a slightly different specific gravity than each of the other balls in the transparent tube so that by noting the number and identity of the balls in the tube which float, a determination can be made as to the strength and therefore the freeze resistance capacity of the radiator solution.

In the prior art, U.S. Pat. No. 398,726 is illustrative of an early form of such a specific gravity testing device. The glass bubbles of this device are flattened into a somewhat disc-like shape. The transparent tubes also have a flattened cross-sectional shape and generally conform to the flattened shape of the disc-like bubbles. One distinct problem of this type of device is that the glass bubbles tend to get hung up on or stuck to the confronting flattened surfaces of the transparent tube.

U.S. Pat. No. 3,055,220 shows another form of hydrometer having a flattened transparent tube. The disc-like float in this device has small knobs or lugs on the float to maintain a spaced relation between the chamber walls and the flat surfaces of the float.

U.S. Pat. No. 1,768,946 shows flat circular floats confined in an enclosed guideway keeping the floats in proper order.

SUMMARY OF THE INVENTION

The antifreeze tester according to the present invention has a transparent tube body in which the floats of various specific gravities are confined and are free to move along the interior guideway. The floats are circular wafer shaped, and the guideway in the transparent tube to accommodate the floats has a generally flattened interior shape generally conforming to the flattened shape of the discs.

The guideway in the transparent tube is provided with a pair of centrally located ribs which extend longitudinally of the guideway and throughout the length thereof. The disc-shaped floats in the guideway are engaged by the ribs so as to be prevented from engaging the broad sidewall surfaces of the guideway in face-to-face relation. Accordingly, the discs in the guideway have minimal engagement with the transparent tube and are therefore free to slide rapidly along the guideway as the solution in the guideway will cause one or more of the floats to tend to float and thereby move along the guideway.

Throughout most of the length of the transparent tube, the tube has an oblong cross-sectional exterior shape. Accordingly, the broad sides of the transparent tube, through which the faces of the disc-shaped floats are seen, is shaped like a lens with a flat inner surface defining one side of the guideway, and a convex outer surface defining the exterior periphery. As a result, the circular disc-shaped wafers appear enlarged as they are viewed through the sidewall of the transparent tube, and accordingly may be more readily seen and identified.

The ribs projecting into the guideway are barely visible through the magnifying sidewall of the tube, and do not obstruct or significantly interfere with the view obtained of the floats in the guideway.

The transparent tube, although flattened throughout most of its length, has cylindrically shaped ends as to accommodate the cylindrical neck or collar of the rubber bulb at one end and the flexible hose at the other end.

BRIEF DESCRIPTION OF THE DRAWINGS

FIG. 1 is an elevation view of the antifreeze tester with portions thereof broken away and shown in section for clarity of detail.

FIG. 2 is an enlarged detail section view taken approximately at 2—2 in FIG. 1.

FIG. 3 is a detail elevation view of the upper end of the transparent tube.

FIG. 4 is an enlarged detail section view taken approximately at 4—4 in FIG. 1.

DETAILED SPECIFICATION

One form of the invention is illustrated in the drawings and is described herein. The tester is indicated in general by numeral 10 and is especially adapted for determining and indicating the specific gravity of liquids such as antifreeze solutions for automotive-type vehicles. Such vehicles have solution in the cooling systems which usually includes ethylene glycol. The solution is kept in the cooling system of the engine all throughout the year for the purpose of preventing freezing of the cooling system during cold winter months, and to minimize the likelihood of overheating the cooling system in the summer months.

The specific gravity tester 10 includes a transparent tube 11, a rubber bulb 12, an end cap 13, and a short length of flexible hose or tube 14. The tester also includes a plurality of circular wafer or disc-shaped floats 15 of varying specific gravities, and a pair of short lengths of flexible plastic tubing 16 serving as obstructions to retain the floats 15 in the interior guideway 17 of the tube.

The tube 11 is of transparent material and must be of a material which is resistive to corrosive influence of various fluids. Although the tube 11 might be formed of glass, the tube 11 is preferably molded of a clear, colorless transparent plastic such as lucite. The tube is constructed by plastic molding.

The opposite end portions 18 of the tube are substantially cylindrical in shape and the intermediate portion 19 between the ends is of oblong or substantially elliptical cross-sectional configuration as clearly depicted in FIG. 2. The cylindrical outer surfaces at the ends 18 of the tube have annular ribs 20 protruding slightly therefrom to fit with a groove 21 in the neck portion of the rubber bulb 12 and to also fit with the annular groove 22 in the end cap 13 so as to minimize the likelihood of the bulb 12 or the end cap 13 from being inadvertently removed from the tube. The neck portion of the bulb 12 and the cylindrical portion of the cap 13 are sized as to tightly grip the ends 18 of the tube so that a liquid and air sealing relation is established between the ends of the tube and the rubber bulb and rubber cap 13.

The cap 13 has a narrow neck portion 23 to receive the hose 14 therein and to retain the hose against inadvertent removal. The cap 13 establishes liquid flow communication between the hose 14 and the interior guideway 17 of the tube.

The guideway 17 in the tube extends throughout the entire length of it and as seen in FIGS. 2 and 4, the guideway 17 has a generally rectangular cross-sectional configuration, and has a width which substantially exceeds the thickness of the guideway.

The elliptical shape of the intermediate portion 19 of tube 11 defines a pair of sidewalls 24 and 25 opposite each other adjacent the guideway 17. Sidewalls 24 and 25 define broad, flat side surfaces 26 extending the full length of the tube. It will be recognized that the broad side surfaces 26 are slightly wider than the diameter of the disc-shaped floats 15 so that there will be an adequate clearance between the floats and the edge surfaces 27 which extend across the thickness of the guideway.

The guideway 17 has a thickness which exceeds, by several times, the thickness of the floats 15 as to define flow channels of significant size which permit the antifreeze solution to freely flow in the guideway during the drawing of a sample into the guideway or discharging the sample from the tube.

The sidewalls 24 and 25 define elongate ribs 28 which project from the side surfaces 26 and inwardly of the guideway 17. The ribs 28 are located opposite each other and in confronting relation with each other throughout the entire length of the guideway, and the ribs 28 have their inner side edges spaced from each other by a distance substantially greater than the thickness of the floats 15, but also substantially less than twice the thickness of the floats. The floats are thereby permitted to slide longitudinally of the tube and between the ribs 28 without obstruction, and the floats are prevented from passing by one another in the guideway 17 and thereby prevented from interchanging their positions in the guideway.

In FIGS. 2 and 4, it will be recognized that the ribs 28 prevent the disc-shaped floats 15 from lying flush against the side surfaces 26, and thereby prevent the floats 15 from sticking to the sidewalls by reason of the surface tension of liquids in the guideway. Accordingly, the ribs 28 contribute materially to the free movability of the floats in the guideway as to prevent any false readings. The smoothly rounded and convexly shaped outer surfaces 29 of sidewalls 24 and 25 provide the walls with a magnifying characteristic so that the circular floats 15 are magnified as they appear through the sidewalls 24 and 25. The magnifying characteristic causes the circular floats to appear as though they are oblong or elliptical in shape, and accordingly, because of the magnified images, the floats may be more readily seen.

Each of the individual floats 15 has a color which is different from the other floats. The specific gravities of the several floats vary from one another and the floats are arranged in the order of their relative specific gravities.

During testing of a sample of antifreeze solution, if the uppermost, or only one, float rises in the solution, then it can be concluded that the solution is safe to approximately 25° F. without freezing; if two of the floats rise in the solution, then it can be concluded that the solution is safe to 5° F.; if three floats rise in the solution and tend to float, then it can be concluded that the solution is safe to a −10° F.; if four of the floats rise in the sample, then the solution is safe to −25° F.; if five of the floats rise, then the solution is safe to −40° F.; and if all of the floats rise, then it must be concluded that the amount of ethylene glycol in the solution is excessive and over-protection is provided.

In use, the hose 14 is extended into the radiator of the engine; and the bulb 12 is simultaneously squeezed and then released to draw a sample of the solution into the tube 11. As the solution which contains some ethylene glycol enters the tube, one or more of the floats 15 will slide upwardly in the guideway. The float will freely move between the ribs 28, and because of the minimal surface engagement between the side surfaces of the floats 15 and the edges of the ribs 28, there will be substantially no restriction to movement of the floats in the guideway. Usually, the floats will start moving upwardly in the tube 11 even before the sample of antifreeze solution completely fills the guideway. As this antifreeze solution is flowing up the guideway, it flows between the side surfaces 26 and the side faces of the floats, and it has been found that the size of the guideway in this configuration, provides ample capacity to quickly receive or discharge the sample of solution. As soon as one or more of the floats 15 moves upwardly in the solution, a state of equilibrium will be reached and at that time the magnified images of the floats will be instantly apparent to a person viewing the floats through the magnifying sidewalls 24 and 25.

By counting the number of disc-shaped floats which have risen toward the top in the solution, a conclusion may be immediately reached as to the strength of the antifreeze solution.

It will be seen that we have provided a new and improved specific gravity tester for antifreeze solutions and the like and utilizing broad and substantially flat disc-shaped floats of varying specific gravities which move freely in the interior guideway of the transparent tube because the inwardly projecting ribs prevent the floats from lying flush against the side surfaces of the guideway, and accordingly, there is no tendency of the floats to stick or otherwise be obstructed in their movement freely along the guideway. The elliptical outer surfaces of the opposite sidewalls of the transparent tube produce a magnifying characteristic in the sidewalls and enlarge the image of the floats so that they may be readily seen and understood.

What is claimed is:

1. A specific gravity tester for liquids such as antifreeze solution for automotive vehicles, comprising
   a transparent tube with a flexible hose on one end and a collapsible suction bulb on the other end,
   a plurality of flat and wafer-like floats of various specific gravities and disposed in the tube, the tube having an interior guideway confining the floats and extending longitudinally of the tube, the guideway having a width substantially greater than thickness to orient all of the wafer-like floats approximately the same therein, the tube defining a pair of substantially broad, flat side surfaces confronting each other and extending across the width of the guideway and also defining a pair of longitudinal edge surfaces across the thickness of the guideway, and the tube also having a pair of elongate ribs in the guideway and extending longitudinally thereof, each of the ribs projecting from a respective side surface in a direction across the thickness of the guideway and each rib being spaced from each edge surface by a distance significantly less than the width of the wafer-like floats, the ribs being spaced from each other by a distance which is significantly more than the thickness of the wafer-like floats and which is also significantly less than twice the thickness of the floats.

2. The specific gravity tester according to claim 1 and the ribs being disposed opposite each other and in confronting relation with each other.

3. The specific gravity tester according to claim 1 and the ribs being disposed intermediate the width of the broad flat side surfaces.

4. The specific gravity tester according to claim 1 and the ribs being disposed substantially equal distances from the edge surfaces and extending throughout substantially the entire length of the guideway.

5. The specific gravity tester according to claim 1 and the tube having an elongate exterior surface which is convexly curved in a direction transversely of the tube and adjacent one of said broad flat side surfaces to impart a magnifying characteristic to the tube through which the wafer-like floats may be seen with a magnified image.

6. A specific gravity tester for liquids such as antifreeze solution for automotive vehicles, comprising
a transparent tube with a flexible hose on one end and a collapsible suction bulb on the other end,
a plurality of flat and wafer-like floats of various specific gravities and disposed in the tube,
the tube having an interior guideway containing the floats and extending longitudinally of the tube, the guideway having a width substantially greater than thickness to orient all of the wafer-like floats approximately the same therein, the tube having a pair of longitudinally extending sidewalls defining elongate and broad interior side surfaces confronting each other and extending across the width of the guideway, said sidewalls also having elongate convexly shaped exterior surfaces extending substantially throughout the length of said guideway whereby to impart a magnifying characteristic to the sidewalls to enlarge the appearance of the floats as seen through the sidewalls.

7. The specific gravity tester according to claim 6 and said wafer-like floats having circular side faces confronting the sidewalls of the tube, said faces of the floats being magnified by said sidewalls to appear oblong or elongated in a direction transversely of the length of the tube.

8. The specific gravity tester according to claim 6 and said tube having a pair of elongate ribs in the guideway and extending longitudinally thereof, said ribs having a thickness substantially less than the thickness of the guideway and thereby preventing the wafer-like floats from lying flush against the broad flat side surfaces of the guideway while permitting unobstructed movement of the floats longitudinally along the tube.

9. A specific gravity tester for liquids such as antifreeze solution for automotive vehicles, comprising
a transparent tube with a flexible hose on one end and a collapsible suction bulb on the other end,
a plurality of flat and wafer-like floats of various specific gravities and disposed in the tube, the floats having circular faces,
the tube having an interior guideway confining the floats and extending longitudinally of the tube, the guideway having a width substantially greater than thickness as to orient all of the wafer-like floats approximately the same therein, the thickness of the guideway being substantially greater than the thickness of the floats as to permit free flow of the liquids longitudinally through the guideway without obstruction, the tube having a pair of broad sidewalls opposite each other and extending longitudinally of the tube with said guideway being disposed between the sidewall, each sidewall of the tube having an inwardly facing broad flat side surface with a longitudinally extending rib thereon projecting into the guideway, the ribs on the opposite sidewalls being spaced from each other a distance substantially greater than the thickness of the wafer-like floats, but substantially less than twice the thickness of said floats as to permit free movement of the floats along the guideway while preventing the floats from interchanging their positions in the guideway, at least one of the sidewalls of the tube having a longitudinally extending exterior surface which is convexly curved in a direction transversely of the tube whereby to impart a magnifying characteristic to the sidewall and produce a magnified image of the circular floats which appear oblong and elongated in a direction transversely of the tube.

10. The specific gravity tester according to claim 9 and said ribs being disposed directly opposite each other and in confronting relation with each other, said ribs having narrow float-engaging edge surfaces with a width considerably less than the width of the side faces of the floats.

* * * * *